United States Patent [19]
Brown et al.

[11] Patent Number: 5,527,830
[45] Date of Patent: Jun. 18, 1996

[54] DRUGS FOR THE TREATMENT OF CARDIAC ARREST AND OTHER SHOCK STATES

[75] Inventors: Charles G. Brown, Columbus, Ohio; Duane D. Miller, Germantown, Tenn.

[73] Assignee: The Ohio State University, Columbus, Ohio

[21] Appl. No.: 312,665

[22] Filed: Sep. 26, 1994

Related U.S. Application Data

[63] Continuation of Ser. No. 119,661, Sep. 13, 1993, abandoned.

[51] Int. Cl.$^6$ .................... A61K 31/135; C07C 211/27
[52] U.S. Cl. .................... 514/605; 514/653; 514/654; 564/99; 564/364; 564/381
[58] Field of Search .................... 514/605, 653, 514/654; 564/99, 364, 381

[56] References Cited

U.S. PATENT DOCUMENTS

| | | | |
|---|---|---|---|
| 3,660,487 | 5/1972 | Larsen et al. | 564/99 X |
| 3,976,695 | 8/1976 | Kaiser et al. | 564/364 X |

OTHER PUBLICATIONS

Burger, A. et al, "Nuclear Substituted 3,4–Dihydroxyphenethylamines and Related Derivatives", *J. Amer. Chem. Soc.*, vol. 78, No. 16, Aug. 1956, pp. 4419–4422.

Brown et al., "Adrenergic agonists during cardiopulmonary resuscitation", *Resuscitation*, vol. 19, 1990, pp. 1–16.

Lindner et al., "Comparison of Different Doses of Epinephrine on Myocardial Perfusion and Resuscitation Success During Cardiopulmonary Resuscitation in a Pig Model", Am. J. Emerg. Med., vol. 9, No. 1, 1991, pp. 27–31.

Gonzalez et al., "Dose–Dependent Vasopressor Response to Epinephrine During CPR in Human Beings", *Ann Emerg Med*, vol. 18:9, Sep. 1989, pp. 920–926.

Callaham et al., "A Randomized Clinical Trial of High–Dose Epinephrine and Norepinephrine vs Standard–Dose Epinephrine in Prehospital Cardiac Arrest", JAMA, vol. 268, No. 19, Nov. 18, 1992, pp. 2667–2672.

Brown et al., "The effects of graded doses of epinephrine on regional myocardial blood flow during cardiopulmonary resuscitation in swine", Circulation, vol. 75, No. 2, Feb. 1987, pp. 491–497.

Brown et al., "Methoxamine versus epinephrine on regional cerebral blood flow during cardiopulmonary resuscitation", *Crit. Care Med*, vol. 15, No. 7, Jul. 1987, pp. 682–686.

Brown et al., "Effect of Standard Doses of Epinephrine on Myocardial Oxygen Delivery and Utilization During Cardiopulmonary Resuscitation", Crit. Care Med., vol. 16, No. 5, May 1988, pp. 536–539.

Brown et al., "Myocardial Oxygen Delivery/Consumption During Cardiopulmonary Resuscitation: A Comparison of Epinephrine and Pheylephrine", Ann Emerg Med, vol. 17:4, Apr. 1988, pp. 302–308.

Brown et al., "The Effect of Epinephrine Versus Methoxamine on Regional Myocardial Blood Flow and Defibrillation Rates Following a Prolonged Cardiorespiratory Arrest in a Swine Model", Am J Emerg Med., vol. 5, No. 5, 1987, pp. 362–369.

Goodman and Gilman (eds.), *The Pharmacological Basis of Therapeutics*, 5th ed., MacMillan Publishing Co., Inc., New York, 1975, p. 482.

*Primary Examiner*—Jacqueline Haley
*Attorney, Agent, or Firm*—Kremblas, Foster, Millard & Pollick

[57] ABSTRACT

The invention relates to new drugs for augmenting perfusion pressure administered during cardiopulmonary resuscitation and other shock states. The compounds include phenylethanolamines and imidazolines, and fluorinated derivatives thereof, which act on adrenergic receptors in patients. The compounds of the invention enhance neurologic outcome and survival, and decrease ventricular dysrhythmias in patients suffering cardiac arrest and other shock states, relative to the outcomes, survival, and post defibrillation ventricular dysrhythmias in conventional therapy for use in resuscitation.

7 Claims, 5 Drawing Sheets

I

II

III

DRUGS FOR THE TREATMENT OF CARDIAC ARREST AND OTHER SHOCK STATES

This is a continuation of application Ser. No. 08/119,661, filed Sep. 13, 1993, now abandoned.

TECHNICAL FIELD

The invention relates to the use of drugs to augment perfusion pressure during cardiopulmonary resuscitation (CPR) and other shock states.

BACKGROUND ART

In the United States alone, approximately 450,000 people yearly suffer a cardiac arrest outside the hospital. Less than 10% of these patients are discharged from the hospital alive, and of these, approximately 60% suffer some form of permanent neurologic injury. The poor outcomes result in part from the low level of myocardial and cerebral blood flow and oxygen delivery generated during standard external CPR following a prolonged cardiopulmonary arrest. While epinephrine, which is an alpha-1,2; beta-1,2 adrenergic agonist, is used during CPR to enhance perfusion, new drugs are needed to optimize hemodynamics and minimize toxicity (i.e., increases in oxygen consumption and ventricular dysrhythmias) in this setting.

Adrenergic agonists are used in CPR to augment cerebral (CePP) and coronary perfusion pressure (CPP). The present inventors have earlier demonstrated an increase in aortic diastolic pressure, the main component of CPP, in animals using nordefrin as compared to epinephrine. Nordefrin also demonstrated similar hemodynamic activity compared to norepinephrine. In addition, none of the animals receiving nordefrin developed hemodynamically significant ventricular dysrhythmias following defibrillation.

The present inventors have also earlier demonstrated improved changes in aortic diastolic pressure using a peripherally acting imidazoline with strong alpha-2 and weak alpha-1 agonist properties and a phenylethanolamine with strong alpha-2 and weak alpha-1 and beta-1 agonist properties.

Redding et al. demonstrated the importance of adrenergic agonists in CPR. In those studies, when adrenergic agonists were added to artificial respiration and closed-chest CPR, myocardial perfusion and resuscitation rates were improved compared to animals receiving CPR alone. Studies by Yakaitis and Otto confirmed these findings and established that it was the alpha agonist component of adrenergic drugs that were primarily responsible for the improvement in myocardial perfusion. By blocking the beta adrenergic agonist components of epinephrine, an alpha 1,2; beta 1,2 agonist, they were able to demonstrate comparable resuscitation rates compared to epinephrine alone, and diminished resuscitation rates when the alpha agonist components of epinephrine were blocked.

In several prior art studies, swine models have been used to simulate out-of-hospital cardiopulmonary arrest in humans. Because of similarities in thoracic and cardiovascular anatomy, swine are recognized as the model species of choice for anticipating the effects of drugs on human hearts during CPR.

One compound, 2-(2,6-diethyl-3-anilino)-2-imidazoline, also known as ST-91, represents the first member of the imidazoline class of adrenergic agonists to show beneficial effects in the swine model of cardiac arrest and CPR. ST-91 is known to be selective for peripheral action on adrenergic receptors. It is believed that the alkyl groups play an important role in preventing ST-91 from getting into the central nervous system and thus only the peripheral actions are observed in contrast to other imidazoline derivatives.

It would therefore be desired to provide improved adrenergic agonists that will enhance the outcome in patients suffering cardiac arrest. Also, drugs currently used to treat cardiac arrest often possess undesirable side effects, such as increased oxygen consumption and post-defibrillation ventricular dysrhythmias. It would be desirable to have a new drug or drugs for the treatment of cardiac arrest and other shock states which do not have these and other adverse side effects.

BRIEF DISCLOSURE OF INVENTION

It is therefore one object of the present invention to provide adrenergic agonists that will improve the outcome in patients suffering cardiac arrest and other shock states.

Another object of the present invention is to provide analogs or derivatives from two distinct classes of adrenergic agonists, phenylethanolamines and imidazolines, that act on adrenergic receptors, with no or reduced adverse effects on the patient, relative to the side effects of conventional drugs used in CPR and other shock states.

Still another object of the present invention is to provide novel compounds that enhance neurologic outcome and survival, and decrease ventricular dysrhythmias, in patients suffering cardiac arrest and other shock states, relative to neurologic outcomes, survival, and post defibrillation ventricular dysrhythmias in conventional therapy for use in CPR and other shock states in humans and other mammals.

Yet another object of the present invention is to provide a method for the treatment of shock states, which as used herein can include among other conditions, cardiac arrest.

Using the knowledge of the structure-activity relationship of adrenergic agonists, the present invention is also directed to the synthesis of novel peripheral alpha-2 agonists in the imidazoline and phenylethanolamine classes.

By the present invention, a comparison of analogs of norepinephrine and peripherally acting imidazolines to norepinephrine can be carried out in a swine model of cardiac arrest and CPR. The compounds of the present invention should maximize CePP and CPP during CPR and other shock states, in mammals and humans, without the use of alpha- and beta-blocking agents which have a substantial vasodepressor effect.

BRIEF DESCRIPTION OF FIGURES

In describing the preferred embodiments of the invention which are illustrated in the Figures, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

According to the present invention, several important structure-activity relationships of adrenergic agonists in the phenylethanolamine class are possible. The substituted phenylethanolamine compounds of the present invention have the following structural similarities: 3,4-hydroxy substitution on the benzene ring (except compound V); hydroxy substitution on the beta carbon (except compounds III and IV); a terminal amino group; and no or minimal substitution on the terminal amino group. Phenylethanolamines with deviation from the above structural requirements have shown minimal or no hemodynamic activity when administered during CPR in the described swine model. For example, methoxamine which lacks the 3,4-hydroxy substitution on the benzene ring has almost no activity in enhancing cerebral and myocardial hemodynamics. In addition, phenylephrine, which only lacks the hydroxy substitution at the 4-position on the benzene ring is more active than methoxamine, but is less active than epinephrine and norepinephrine in this swine model.

Figure 1:
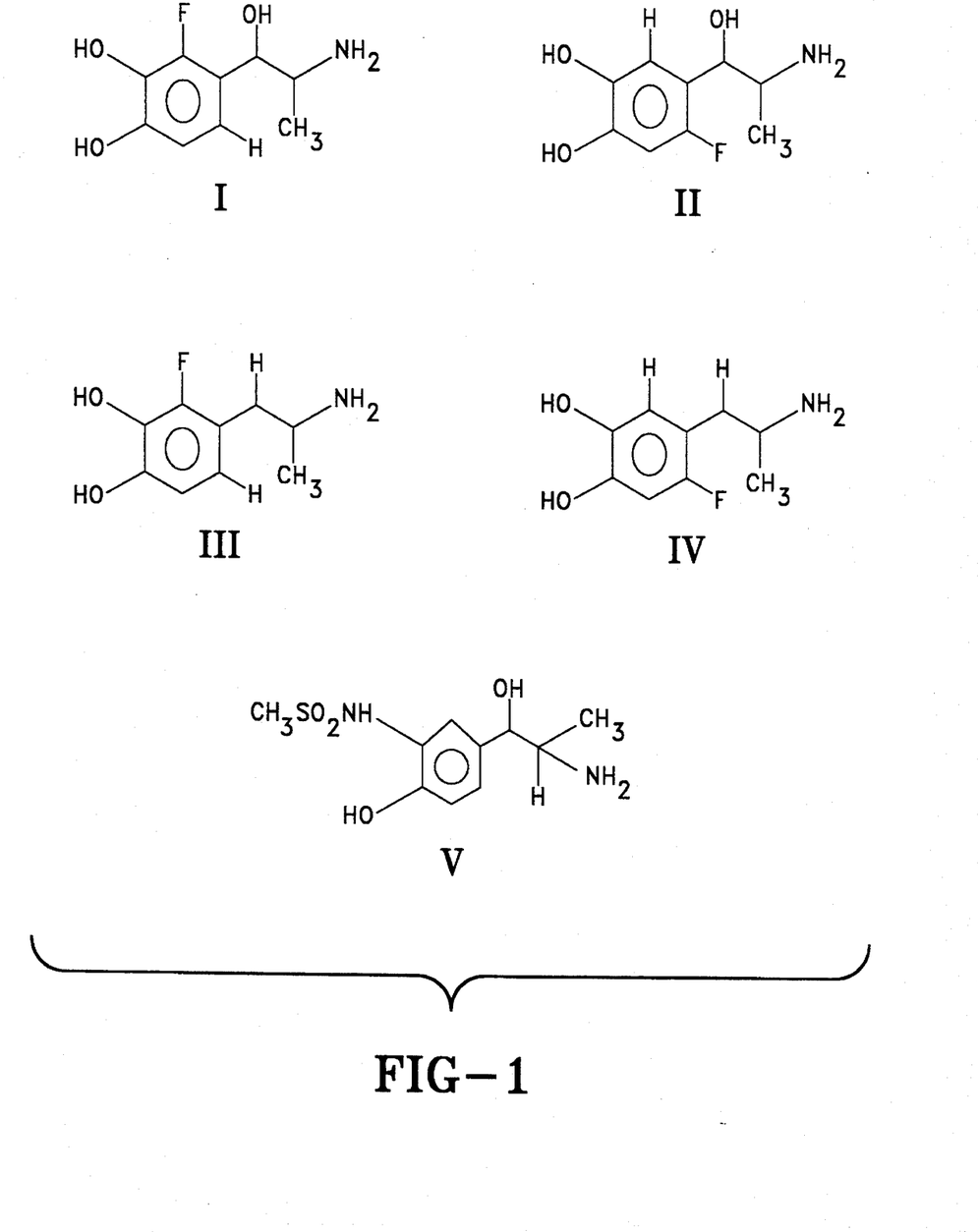
FIG. 1 illustrates the structures of substituted phenylethanolamine compounds I, II, III, IV, and V.
Figure 2:
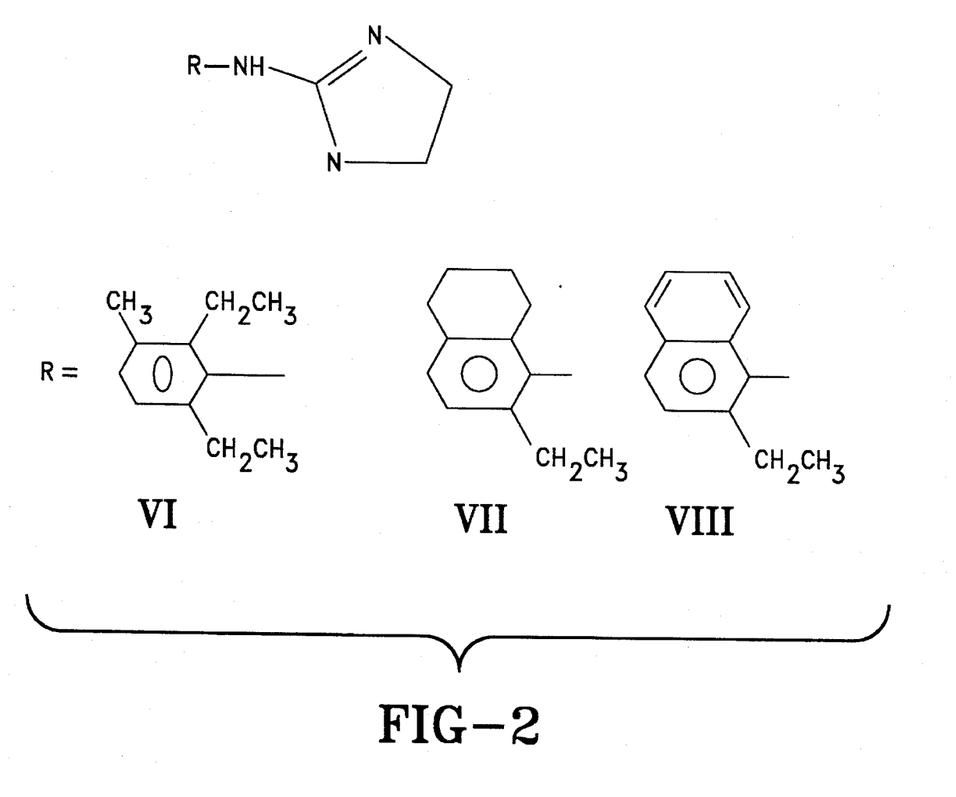
FIG. 2 illustrates the structures of substituted imidazoline compounds VI, VII, and VIII.
Figure 3:
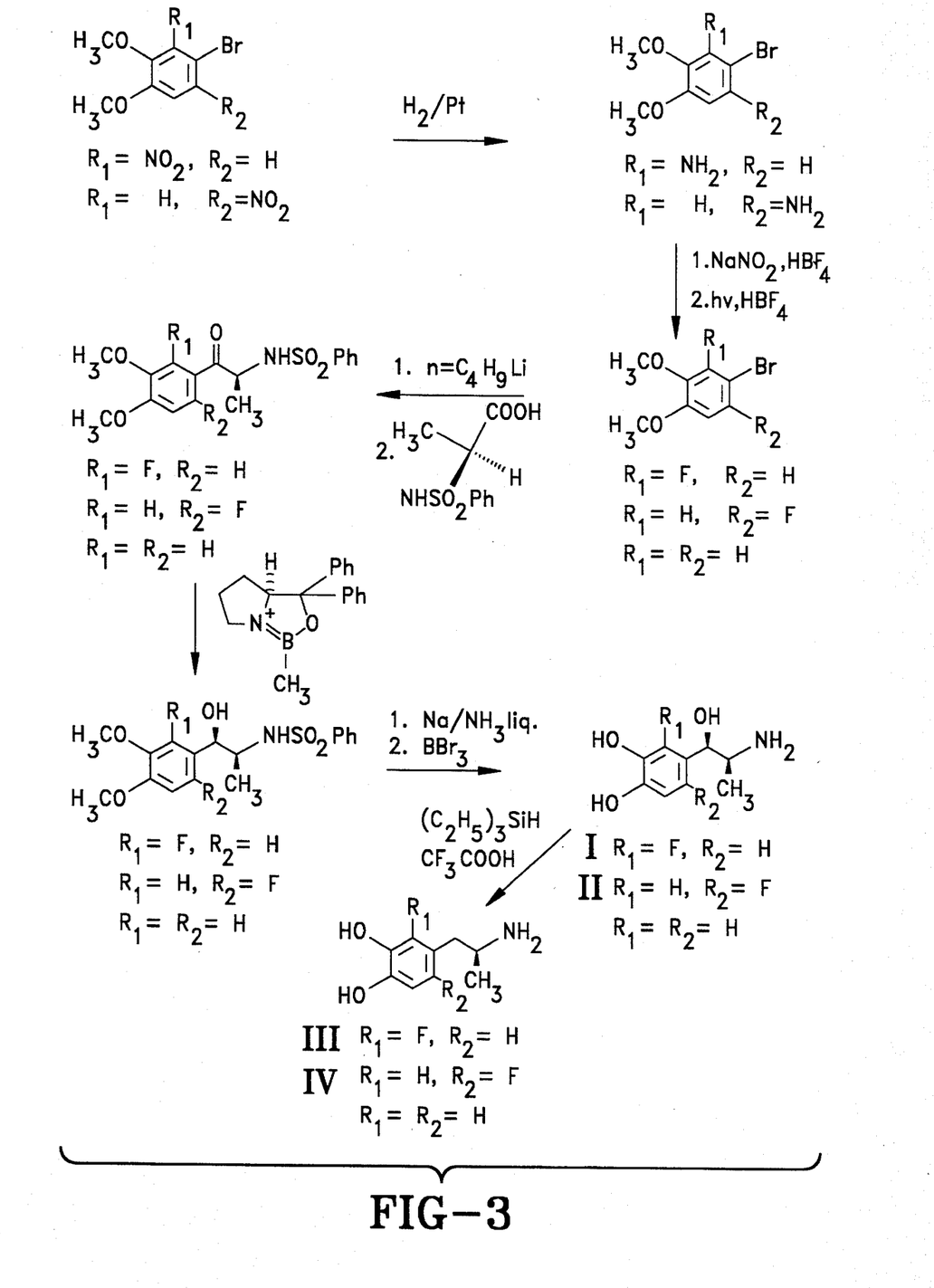
FIG. 3 illustrates the synthesis of compounds I, II, III, and IV.
Figure 4:
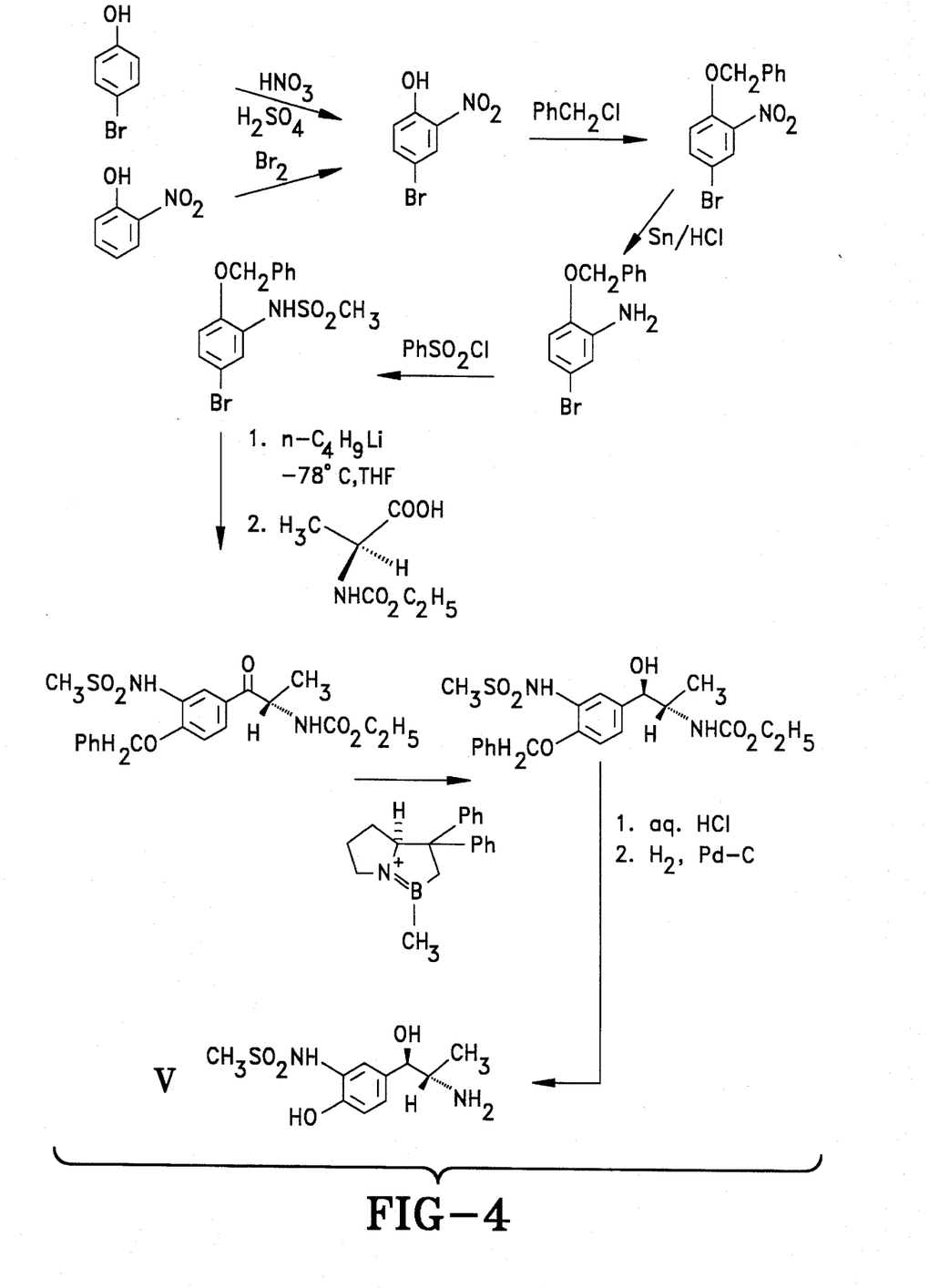
FIG. 4 illustrates the synthesis of compound V.
Figure 5:
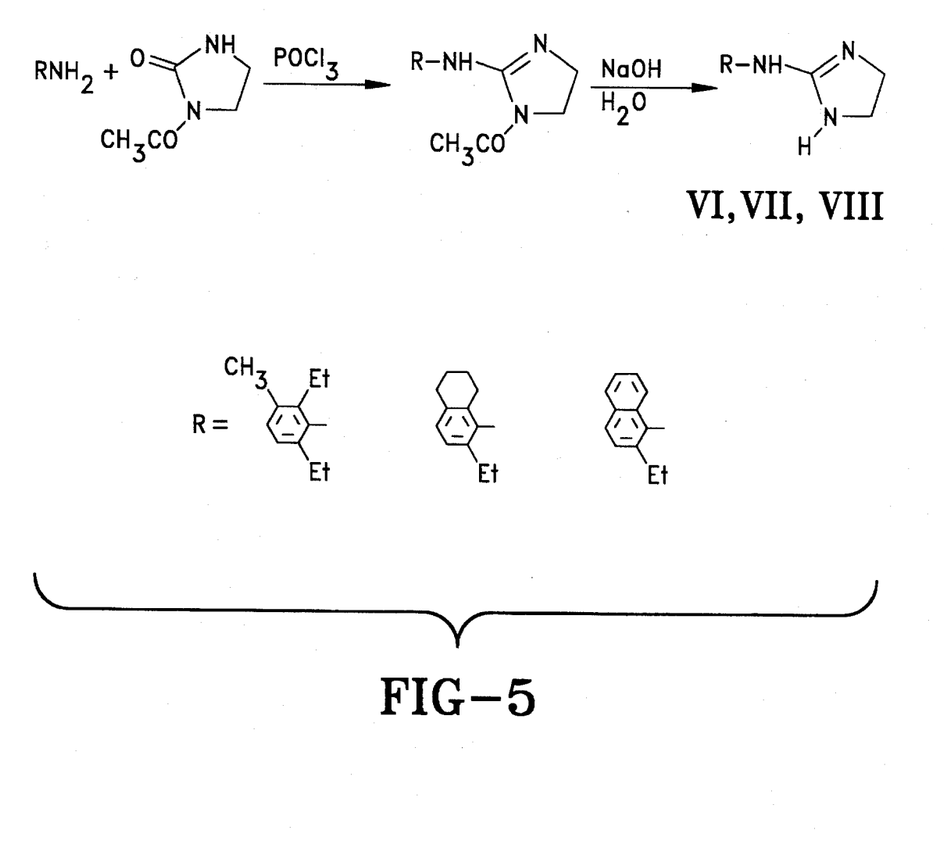
FIG. 5 illustrates the synthesis of compounds VI, VII, and VIII.

While it is known that it is important to maintain the 2,6-carbon substitution on the imidazoline analogs, the present invention shows in FIGS. 3–5 the structures of novel substituted compounds with enhanced alpha-2 activity relative to alpha-1 adrenergic activity by also placing a substituent in the 3 position (FIG. 2).

It has thus been shown by the present invention that changing the configuration of, or the type of substitution on, the structure of certain phenylethanolamine analogs and imidazoline analogs provides compounds with significant improvement in alpha- and beta-adrenergic activity on adrenergic receptor sites, relative to the activity of conventional compounds.

The substituted phenylethanolamine and substituted imidazoline compounds of the present invention should also improve the cerebral and myocardial hemodynamics of subjects experiencing a cardiac arrest and other shock states, relative to the results from the use of no cardiac drugs (when indicated), or relative to cardiac arrest therapy using conventional drugs, such as epinephrine, norepinephrine, and the like. In this manner, the administration of the compounds of the present invention to a subject experiencing cardiac arrest, and other shock states, should improve the outcome of said subject, relative to the outcome of patients treated with conventional drugs or no drugs.

Thus the present invention also relates to a phenylethanolamine derivative compound selected from the group consisting of (alpha S, beta R)-alpha-(1-aminoethyl)-2-fluoro-3,4-dihydroxybenzenemethanol (see compound I); (alpha S, beta R)-alpha-(1-aminoethyl)-2-fluoro-4,5-dihydroxybenzenemethanol (see compound II); (alpha S)-alpha-methyl-2-fluorodopamine (see compound III); (alpha S)-alpha-methyl-6-fluorodopamine (see compound IV); and (alpha S, beta R)-alpha-(1-aminoethyl)-4-hydroxy-3-methanesulfonamido-benzenemethanol (see compound V), which should enhance outcome and decrease toxicity, oxygen consumption, and ventricular dysrhythmias, in mammals or human patients suffering cardiac arrest and other shock states, relative to outcomes, toxicity, oxygen consumption, and post defibrillation ventricular dysrhythmias in conventional therapy for use in CPR and other shock states.

The preferred substituted phenylethanolamine compound of the present invention for improving perfusion pressure during CPR in humans is compound I.

It is thus evident from the present invention that the preferred substituted phenylethanolamines contain fluorine substitution on the phenol ring in the position adjacent to the bonding site on the ring of the ethanolamine moiety. The fluorine atom on the molecules of compounds I–IV is believed to impart selective action for adrenergic receptors. The compounds can contain fluorine substituents on both of the phenol ring positions immediately adjacent to the bonding site on the ring of the ethanolamine moiety.

The present invention demonstrates the importance of the intact catechol segment of the phenylethanolamines for activity on adrenergic receptor sites. Furthermore, in another preferred embodiment of the present invention, the methanesulfonamido group ($-NHSO_2CH_3$) of compound V can replace a phenolic hydroxyl group of the norepinephrine and derivative compound V retains adrenergic activity similar to that of norepinephrine, but yet is not metabolized by catechol O-methyl transferase, one of the main routes of metabolism for epinephrine. This should allow for the use of a much smaller dose of compound V needed to achieve the desired hemodynamic effect when used in mammals such as swine or humans, relative to the dose of epinephrine required to achieve comparable results.

Imidazoline analogs (VI, VII, VIII) of the present invention should act on peripheral alpha-adrenergic receptor sites to potentially enhance hemodynamics in cardiac arrest and CPR and other shock states, without producing undesired dysrhythmias or other toxicities. Comparable effective treatment of subjects experiencing cardiac arrest or other shock states is indicated.

The present invention therefore also relates to an imidazoline compound selected from the group consisting of 2-(2,6-diethyl-3-methylanilino)-2-imidazoline (see compound VI); 2-(2[ethyl-5,6,7,8-tetrahydronaphthylamino)-2-imidazoline (see compound VII); and 2-(2-ethylnaphthylamino)-2-imidazoline (see compound VIII), which should enhance outcome and decrease toxicity, and oxygen consumption, in mammals and human patients suffering cardiac arrest and other shock states, relative to outcomes, toxicity, and oxygen consumption in conventional therapy for use in CPR and other shock states.

Shock is a condition the human body enters during periods of poor organ perfusion, which could be caused by a number of conditions. The effect of shock on the human body is to drastically reduce the amount of available circulating blood, oxygen and nutrients, for perfusion of the critical organs. Thus the present invention is directed to a method to constrict peripheral circulation in subjects suffering cardiac arrest and other shock states, whereby the cerebral and myocardial perfusion are increased, said method comprising administering to the subject a sufficient amount of a compound selected from the group consisting of (alpha S, beta R)-alpha-(1-aminoethyl)-2-fluoro-3,4-dihydroxybenzenemethanol (see compound I); (alpha S, beta R)-alpha-(1-aminoethyl)-2-fluoro-4,5-dihydroxybenzenemethanol (see compound II); (alpha S)-alpha-methyl-2-fluorodopamine (see compound III); (alpha S)-alpha-methyl-6-fluorodopamine (see compound IV); and (alpha S, beta R)-alpha-(1-aminoethyl)-4-hydroxy-3-methanesulfonamido-benzenemethanol (see compound V), and 2-(2,6-diethyl-3-anilino)-2-imidazoline, also known as ST-91, whereby the peripheral circulation is decreased and cerebral and myocardial perfusion is enhanced.

The invention also relates to a method to constrict peripheral circulation in subjects suffering cardiac arrest and other shock states, whereby cerebral and myocardial perfusion are enhanced, said method comprising administering to the subject a sufficient amount of a compound selected from the group consisting of 2-(2,6-diethyl-3-methylanilino)-2-imidazoline; 2-(2[ethyl-5,6,7,8-tetrahydronaphthylamino)-2-imidazoline; and 2-(2-ethylnaphthylamino)-2-imidazoline, (compounds VI–VIII), whereby the peripheral circulation is decreased and cerebral and myocardial perfusion is enhanced.

It is believed that the drugs of the present invention are useful in augmenting perfusion pressure during shock, cardiac arrest and CPR of humans and other mammals with adrenergic receptor sites because of improved binding to the adrenergic receptor sites as a result of the substituent and configurational changes of the drugs of the present invention relative to the structure of norepinephrine.

The present invention further relates to a method for treating cardiac arrest and other shock states in a mammal suffering cardiac arrest or other shock states. The mammal suffering cardiac arrest or other shock states which can benefit from the present invention can be, for example, a swine or a human, but the present invention is not limited to the treatment of these species and can include all mammals with adrenergic receptor sites responsive to compounds I–VIII and 2-(2,6-diethyl-3-anilino)-2-imidazoline, also known as ST-91.

The preferred treatment method herein comprises administering to the mammal suffering cardiac arrest or other shock states an amount of ST-91, or a substituted phenylethanolamine compound, or a substituted imidazoline compound sufficient to enhance resuscitation. The administration of the compound can be by intravenous, intratracheal, intracardiac, intraosseous, intralingual, intranasal, and intraarterial injection but the preferred method is intravenous injection into a subject experiencing cardiac arrest or other shock states. The preferred substituted phenylethanolamine for the treatment method of the present invention is compound I. Other substituted phenylethanolamines useful in the treatment method of the present invention include compounds II through V.

The preferred substituted imidazoline for the treatment method of the present invention is compound VI. Other substituted imidazolines useful in the treatment method of the present invention include 2-(2[ethyl-5,6,7,8-tetrahydronaphthylamino)-2-imidazoline (compound VII); and 2-(2-ethylnaphthylamino)-2-imidazoline (compound VIII).

The preferred substituted imidazoline compound of the present invention for improving perfusion pressure during cardiac arrest and other shock states in humans and other mammals is compound VI.

It is believed that the amount of substituted phenylethanolamine compound of the present invention needed according to the method of the present invention to achieve augmentation of perfusion pressure during CPR or the treatment of other shock states is, for example, in the range of from about 0.02 to about 3.2 milligrams of the substituted phenylethanolamine compound per kilogram of patient body mass. However, this range is not a limitation herein and any effective and non-toxic dose of the substituted phenylethanolamine compound of the present invention is useful in the method of the present invention.

It is believed that the amount of substituted imidazoline compound of the present invention needed according to the method of the present invention to achieve augmentation of perfusion pressure during CPR or the treatment of other shock states is, for example, in the range of from about 0.02 to about 2.0 milligrams of substituted imidazoline compound per kilogram of patient body mass. However, this range is not a limitation herein and any effective and non-toxic dose of the substituted imidazoline compound of the present invention is useful in the method of the present invention.

It is therefore believed that the novel compounds of the present invention and ST-91 provide improved treatment of cardiac arrest and other shock states because the compounds are more effective at enhancing perfusion pressure during CPR than are epinephrine and norepinephrine, conventionally administered drugs during CPR. Furthermore, the use of ST-91 or substituted phenylethanolamines and substituted imidazolines of the present invention should not induce the undesirable levels of toxicity, increases in oxygen consumption, or post defibrillation ventricular dysrhythmias seen with conventional drugs used in cardiac arrest and other shock states. In addition, the compounds of the present invention are believed to have enhanced adrenergic receptor binding affinities in tissues of swine and humans, relative to the binding affinities of conventional drugs used in cardiac arrest and other shock states. Finally, the use of ST-91 or the substituted compounds of the present invention should improve the outcome in patients suffering cardiac arrest and other shock states, relative to the outcome from conventional drugs.

EXAMPLE 1

Synthesis of Compound I. (alpha S, beta R)-alpha-(1-aminoethyl)-2-fluoro-3,4-dihydroxybenzenemethanol. (See FIG. 3)

A starting compound of 1,2-dimethoxy, 3-nitro,4-bromobenzene is treated with reduction conditions of hydrogen and platinum catalyst to reduce the nitro group to an amine. This reaction product is treated with sodium nitrite and hydrofluoroborate ($HBF_4$), followed by irradiation and more $HBF_4$ to substitute a fluorine on the ring for the amine group in the three position. This product is treated with n-butyl lithium followed by S(N-phenylsulfonyl)alanine to produce the ketone. This ketone intermediate is then treated with a mild reducing agent, diborane, to reduce the carbonyl to a secondary alcohol group. This compound is then treated with sodium in liquid ammonia followed by boron tribromide to remove the $SO_2Ph$ group and also reduce the methoxy groups to hydroxyls, whereby the name compound (I) is produced.

EXAMPLE 2

Synthesis of Compound II. (alpha S, beta R)-alpha-(1-aminoethyl)-2-fluoro-4,5-dihydroxybenzenemethanol. (See FIG. 3 )

A starting compound of 1,2-dimethoxy, 4-nitro,5-bromobenzene is treated with reduction conditions of hydrogen and platinum catalyst to reduce the nitro group to an amine. This reaction product is treated with sodium nitrite and hydrofluoroborate ($HBF_4$), followed by irradiation and more $HBF_4$ to substitute a fluorine on the ring for the amine group in the four position. This product is treated with n-butyl lithium followed by S(N-phenylsulfonyl)alanine to produce the desired ketone. This intermediate is then treated with a mild reducing agent, diborane with chiral oxazaborolidine, to reduce the carbonyl to a secondary alcohol group. This compound is then treated with sodium in liquid ammonia followed by boron tribromide to remove the $SO_2Ph$ group and also reduce the methoxy groups to hydroxyls, whereby the name compound (II) is produced.

EXAMPLE 3

Synthesis of (III) (alpha S)-alpha-methyl-2-fluorodopamine. (See FIG. 3)

Compound I, produced by the method of Example 1, is treated with triethyl silane and trifluoro acetic acid to remove the secondary alcohol group, whereby the name compound (III) is produced.

EXAMPLE 4

Synthesis of (IV) (alpha S)-alpha-methyl-6-fluorodopamine. (See FIG. 3)

Compound II, produced by the method of Example 2, is treated with triethyl silane and trifluoro acetic acid to remove the secondary alcohol group, whereby the name compound (IV) is produced.

EXAMPLE 5

Synthesis of Compound V. (alpha S, beta R)-alpha-(1-aminoethyl)-4-hydroxy-3-methanesulfonamidobenzenemethanol. (See FIG. 4)

A starting compound of p-bromophenol is nitrated with nitric acid/sulfuric acid to produce o-nitro,p-bromo phenol. Alternatively, this can be prepared by the bromination in the para position of o-nitro phenol. The o-nitro,p-bromo phenol is reacted with PhCH2Cl to convert the hydroxyl on the ring to —OCH$_2$Ph. This product is reduced with tin and hydrochloric acid to convert the nitro group to an amine, followed by reaction with methane sulfonyl chloride to convert the aromatic amine group to —NHSO$_2$CH$_3$. Treatment with n-butyl lithium in cold tetrahydrofuran followed by reaction with S(N-carboethoxyl)alanine produces the desired ketone. Mild reduction of this intermediate with diborane with chiral oxazaborolidines reduces the carbonyl group to a secondary alcohol. This material is treated with aqueous hydrochloric acid followed by reduction with hydrogen over palladium catalyst to yield the name compound (V).

EXAMPLE 6

Synthesis of (VI) 2-(2,6-diethyl-3-methylanilino)-2-imidazoline. (See FIG. 5)

2,6-Diethyl-3-methyl aniline is reacted with N-acetyl-2-imidazolidinone in the presence of POCl$_3$ to produce the imidazoline. This intermediate is treated with sodium hydroxide and water to remove the acetyl group and yield the name compound (VI).

EXAMPLE 7

Synthesis of (VII) 2-(2[ethyl-5,6,7,8-tetrahydronaphthylamino)-2-imidazoline. (See FIG. 5)

2-Ethyl-5,6,7,8-tetrahydronaphthyl amine is reacted with N-acetyl-2-imidazolidinone in the presence of POCl$_3$ to produce the imidazoline intermediate. This intermediate is treated with sodium hydroxide and water to remove the aceto group and yield the name compound (VII).

EXAMPLE 8

Synthesis of (VIII) 2-(2-ethylnaphthylamino)-2-imidazoline. (See FIG. 5)

2-Ethylnaphthyl amine is reacted with N-acetyl-2imidazolidinone in the presence of POCl$_3$ to produce the imidazoline intermediate. This intermediate is treated with sodium hydroxide and water to remove the aceto group and yield the name compound (VIII).

EXAMPLE 9

Swine weighing approximately 20–25 Kg each are anesthetized with 5% halothane and oxygen. After tracheostomy, the halothane is reduced to 1.5%, and the animals are instrumented for cerebral and myocardial blood flow measurements. In addition, catheters are placed in: (1) the ascending aorta and right atrium for measurement of aortic and right atrial pressures and arterial blood gases, and (2) coronary sinus and sagittal sinus for determination of sagittal and coronary sinus blood gases and (3) a 4 F bipolar pacing wire in the right ventricle for the induction of ventricular fibrillation. A fluid-filled catheter is placed through the external jugular vein into the superior vena cava for drug administration. Following 10 minutes of ventricular fibrillation, CPR is begun. Following 3 minutes of CPR, the animals are allocated to receive 0.02 mg/Kg to 3.2 mg/Kg of one of compounds I–V or ST-91. Blood flow, oxygen consumption/delivery, aortic diastolic pressure, rates of ventricular dysrhythmias, and coronary perfusion pressure are then measured in these animals. The results should demonstrate improved myocardial and cerebral hemodynamics, and decreased toxicity, during CPR with the use of the substituted phenylethanolamines or ST91, new therapeutic adrenergic agonists for use in CPR and other shock states.

EXAMPLE 10

Swine weighing approximately 20–25 Kg each are instrumented for cerebral and myocardial hemodynamic measurements as discussed in Example 9. Following 10 minutes of ventricular fibrillation, CPR is begun. Following 3 minutes of CPR, the animals are allocated to receive 0.2 mg/Kg to 2.0 mg/Kg of one of compounds VI–VIII. Blood flow, oxygen consumption/delivery, rates of ventricular dysrhythmias, aortic diastolic pressure, and coronary perfusion pressure are then measured in these animals. The results should demonstrate improved cerebral and myocardial hemodynamics, and decreased toxicity during CPR with the use of the substituted imidazolines, new therapeutic adrenergic agonists for use in CPR and other shock states.

While certain preferred embodiments of the present invention have been disclosed in detail, it is to be understood that various modifications may be adopted without departing from the spirit of the invention or scope of the following claims.

We claim:

1. A substituted phenylethanolamine compound with the structure

2. A substituted phenylethanolamine compound with the structure

IV

3. A composition comprising the compound (alpha S)-alpha-methyl-2-fluorodopamine of claim 1 in combination with a pharmaceutically acceptable carrier, wherein, when the composition is administered to a mammal experiencing a shock state, the peripheral alpha-2 activity in the mammal is enhanced relative to alpha-1 activity, resulting in improved hemodynamics.

4. A composition comprising the compound (alpha S)-alpha-methyl-6-fluorodopamine of claim 2 in combination with a pharmaceutically acceptable carrier, wherein, when the composition is administered to a mammal experiencing a shock state, the peripheral alpha-2 activity in the mammal is enhanced relative to alpha-1 activity, resulting in improved hemodynamics.

5. A method for treating a shock state in a mammal suffering said shock state comprising administering to the mammal in combination with a pharmaceutically acceptable carrier an amount of a compound selected from the group consisting of (alpha S, beta R)-alpha-(1-aminoethyl)-2-fluoro-3,4-dihydroxybenzenemethanol; (alpha S, beta R)-alpha-(1-aminoethyl)-2-fluoro-4,5-dihydroxybenzenemethanol; (alpha S)-alpha-methyl-2-fluorodopamine; (alpha S)-alpha-methyl-6-fluorodopamine; and (alpha S, beta R)-alpha-(1-aminoethyl)-4-hydroxy-3-methanesulfonamido-benzenemethanol sufficient to enhance resuscitation and outcome.

6. The method of claim 5 wherein the administration of the compound is by a means selected from the group consisting of intravenous, intra-arterial, intratracheal, intracardiac, intralingual, intranasal, and intraosseous injection.

7. A method to constrict peripheral circulation in subjects suffering shock, whereby the cerebral and myocardial perfusion are enhanced, said method comprising administering to the subject a sufficient amount of a compound selected from the group consisting of (alpha S, beta R)-alpha-(1-aminoethyl)-2-fluoro-3,4-dihydroxybenzenemethanol; (alpha S, beta R)-alpha-(1-aminoethyl)-2-fluoro-4,5-dihydroxybenzenemethanol; (alpha S)-alpha-methyl-2-fluorodopamine; (alpha S)-alpha-methyl-6-fluorodopamine; and (alpha S, beta R)-alpha-(1-aminoethyl)-4-hydroxy-3-methanesulfonamido-benzenemethanol.

* * * * *